(12) United States Patent
Sanders

(10) Patent No.: US 10,744,315 B2
(45) Date of Patent: Aug. 18, 2020

(54) CONNECTOR FOR SYSTEM FOR CLOSED TRANSFER OF FLUIDS

(71) Applicant: Becton Dickinson and Company Limited, Dun Laoghaire (IE)

(72) Inventor: Laurie Sanders, Glen Ridge, NJ (US)

(73) Assignee: Becton Dickinson and Company Limited (IE)

( * ) Notice: Subject to any disclaimer, the term of this patent is extended or adjusted under 35 U.S.C. 154(b) by 207 days.

(21) Appl. No.: 15/871,344

(22) Filed: Jan. 15, 2018

(65) Prior Publication Data
US 2018/0200498 A1 Jul. 19, 2018

Related U.S. Application Data

(60) Provisional application No. 62/447,046, filed on Jan. 17, 2017.

(51) Int. Cl.
| A61M 39/10 | (2006.01) |
| A61J 1/14 | (2006.01) |
| A61J 1/20 | (2006.01) |
| A61J 1/18 | (2006.01) |

(52) U.S. Cl.
CPC ........ *A61M 39/1011* (2013.01); *A61J 1/1406* (2013.01); *A61J 1/2055* (2015.05); *A61J 1/2065* (2015.05); *A61J 1/2089* (2013.01); *A61J 1/2096* (2013.01); *A61J 1/18* (2013.01); *A61J 1/2058* (2015.05); *A61J 2205/20* (2013.01); *A61M 2039/1072* (2013.01)

(58) Field of Classification Search
CPC .. A61M 2039/1016; A61M 2039/1027; A61M 39/1011; A61M 2039/1072; A61J 1/1406; A61J 1/2048
See application file for complete search history.

(56) References Cited

U.S. PATENT DOCUMENTS

| 4,436,125 A | 3/1984 | Blenkush |
| 4,564,054 A | 1/1986 | Gustavsson |
| 4,576,211 A | 3/1986 | Valentini et al. |
| 5,104,158 A | 4/1992 | Meyer et al. |

(Continued)

FOREIGN PATENT DOCUMENTS

| CN | 104902863 A | 9/2015 |
| CN | 105142594 A | 12/2015 |
| WO | 2012117648 A1 | 9/2012 |

*Primary Examiner* — Bradley J Osinski
(74) *Attorney, Agent, or Firm* — The Webb Law Firm

(57) ABSTRACT

A system for closed transfer of fluids includes a syringe adapter including a cannula having a first end and a second end with the second end positioned within the housing, and a seal arrangement positioned within the housing and movable within the housing with the seal arrangement including a membrane. The system including a second component including a membrane and a locking mechanism. The second component configured to be received by the syringe adapter such that the membrane of the seal arrangement engages the membrane of the second component. The locking mechanism including a biasing member and an engagement member positioned on the biasing member, with the engagement member configured to engage a portion of the housing of the syringe adapter to secure the second component to the syringe adapter when the second component is received by the syringe adapter.

18 Claims, 16 Drawing Sheets

(56) References Cited

U.S. PATENT DOCUMENTS

| | | | |
|---|---|---|---|
| 5,122,123 A * | 6/1992 | Vaillancourt | A61M 39/14 604/192 |
| 5,492,147 A | 2/1996 | Challender et al. | |
| 5,810,792 A | 9/1998 | Fangrow, Jr. et al. | |
| 6,423,053 B1 * | 7/2002 | Lee | A61M 39/1011 604/523 |
| 7,648,491 B2 | 1/2010 | Rogers | |
| 7,975,733 B2 | 7/2011 | Horppu et al. | |
| 8,122,923 B2 | 2/2012 | Kraus et al. | |
| 8,196,614 B2 | 6/2012 | Kriheli | |
| 8,267,127 B2 | 9/2012 | Kriheli | |
| D708,518 S | 7/2014 | Ivosevic | |
| 8,790,327 B2 | 7/2014 | Takemoto | |
| D710,196 S | 8/2014 | Ivosevic | |
| 9,126,029 B2 | 9/2015 | Fangrow et al. | |
| 9,168,366 B2 | 10/2015 | Fangrow et al. | |
| 9,381,137 B2 | 7/2016 | Garfield et al. | |
| 9,414,990 B2 | 8/2016 | Ivosevic et al. | |
| 9,414,991 B2 | 8/2016 | Sanders et al. | |
| 9,510,997 B2 | 12/2016 | Kriheli et al. | |
| 9,597,260 B2 | 3/2017 | Ivosevic et al. | |
| 9,610,222 B2 | 4/2017 | Kriheli et al. | |
| 9,636,278 B2 | 5/2017 | Sanders et al. | |
| 9,642,775 B2 | 5/2017 | Sanders et al. | |
| 9,724,269 B2 | 8/2017 | Sjogren et al. | |
| 9,750,926 B2 | 9/2017 | Lopez et al. | |
| 9,814,871 B2 | 11/2017 | Wlodarczyk et al. | |
| 9,833,605 B2 | 12/2017 | Sanders et al. | |
| 9,855,192 B2 | 1/2018 | Kim et al. | |
| 2009/0069783 A1 * | 3/2009 | Ellstrom | A61M 39/10 604/415 |
| 2013/0006211 A1 | 1/2013 | Takemoto | |
| 2013/0076019 A1 | 3/2013 | Takemoto | |
| 2014/0074038 A1 | 3/2014 | Ivosevic | |
| 2014/0150925 A1 | 6/2014 | Sjogren et al. | |
| 2014/0261877 A1 | 9/2014 | Ivosevic et al. | |
| 2014/0276649 A1 | 9/2014 | Ivosevic et al. | |
| 2015/0297454 A1 | 10/2015 | Sanders et al. | |
| 2015/0297456 A1 | 10/2015 | Marici et al. | |
| 2015/0297459 A1 | 10/2015 | Sanders | |
| 2015/0297839 A1 | 10/2015 | Sanders et al. | |
| 2015/0297881 A1 | 10/2015 | Sanders et al. | |
| 2016/0136412 A1 | 5/2016 | McKinnon et al. | |
| 2016/0271017 A1 | 9/2016 | Weir et al. | |
| 2016/0331637 A1 | 11/2016 | Sanders et al. | |
| 2016/0361504 A1 | 12/2016 | Kim et al. | |
| 2017/0258682 A1 | 9/2017 | Kriheli | |
| 2018/0028402 A1 | 2/2018 | Kriheli et al. | |
| 2018/0071506 A1 | 3/2018 | Sanders et al. | |
| 2018/0085286 A1 | 3/2018 | Kim et al. | |

\* cited by examiner

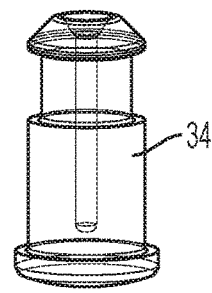 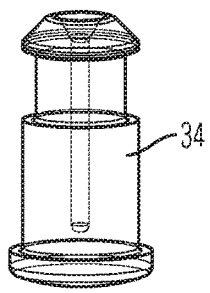 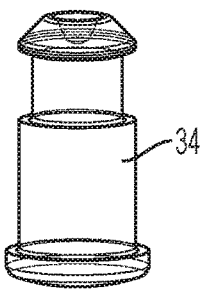 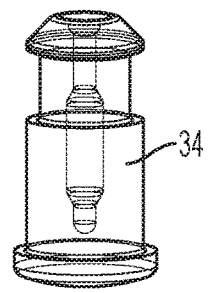
FIG. 7A     FIG. 8A     FIG. 9A     FIG. 10A
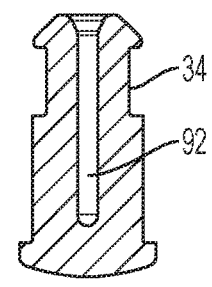 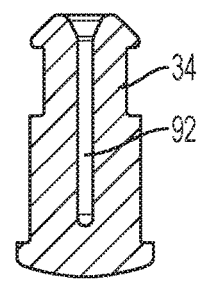 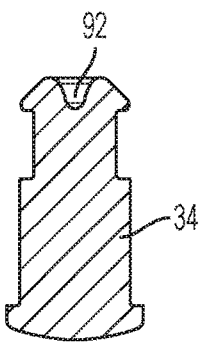 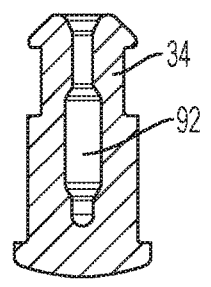
FIG. 7B     FIG. 8B     FIG. 9B     FIG. 10B

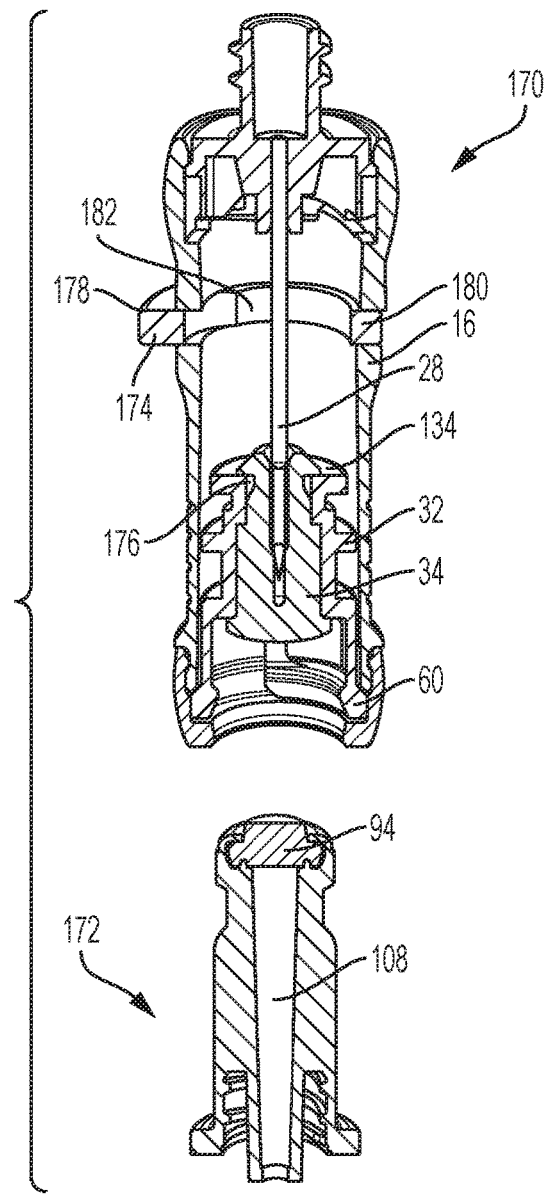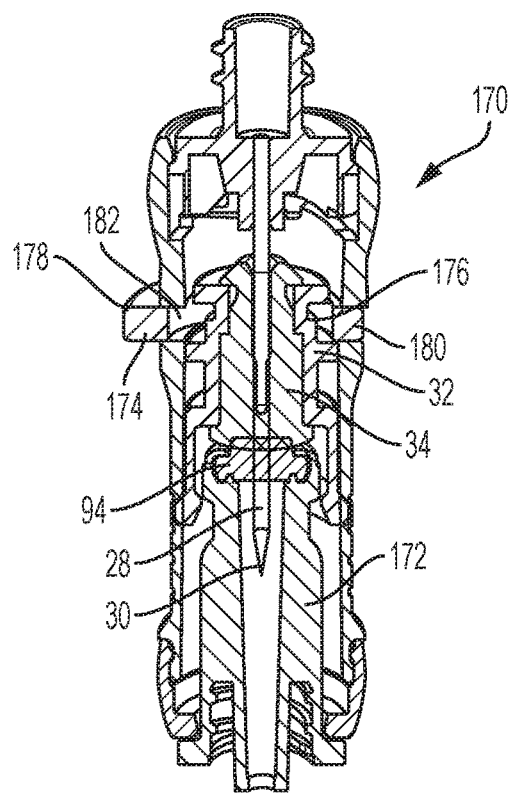
FIG. 31
FIG. 32

_US 10,744,315 B2_

CONNECTOR FOR SYSTEM FOR CLOSED TRANSFER OF FLUIDS

CROSS-REFERENCE TO RELATED APPLICATION

This application claims priority to U.S. Provisional Application Ser. No. 62/447,046, filed Jan. 17, 2017, which is hereby incorporated by reference in its entirety.

BACKGROUND OF THE INVENTION

Field of the Disclosure

The present disclosure relates generally to a system for the closed transfer of fluids. More particularly, the present disclosure relates to a system that provides leak-proof sealing during fluid transfer from a first container to a second container.

Description of the Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists.

SUMMARY OF THE INVENTION

In one aspect, a system for closed transfer of fluids includes a syringe adapter including a housing having a first end and a second end with the first end configured to be secured to a first container, a cannula having a first end and a second end with the second end positioned within the housing, and a seal arrangement positioned within the housing and movable within the housing with the seal arrangement including a membrane. The system including a second component including a membrane and a locking mechanism. The second component configured to be received by the syringe adapter such that the membrane of the seal arrangement engages the membrane of the second component. The locking mechanism including a biasing member and an engagement member positioned on the biasing member, with the engagement member configured to engage a portion of the housing of the syringe adapter to secure the second component to the syringe adapter when the second component is received by the syringe adapter.

The biasing member of the locking mechanism may be a cantilever arm and the engagement member may be a projection extending radially outward from the second component, with the projection configured to engage a portion of the housing to bias the projection radially inward via the cantilever arm during insertion of the second component into the syringe adapter. The projection configured to return to a non-biased position when the second component has been fully inserted into the syringe adapter to secure the second component to the syringe adapter. The seal arrangement may include a collet having a first end and a second end, with at least a portion of the collet received within the housing. The collet may include a body and a locking member connected to the body, with the body defining a passageway that receives the membrane of the seal arrangement. The collet may be movable from a first position where the locking member is open to receive a mating connector to a second position where radially outward movement of the locking member is restricted. The second component may include a collet interface surface configured to receive and engage the locking member of the collet. The locking member may be arcuate-shaped and resilient, with the locking member connected to the body via a plurality of arms. The second component may be a patient connector having a first end and a second end, with the patient connector having a body defining a passageway and the second end of the patient connector configured to be secured to a patient IV line.

In a further aspect, a system for closed transfer of fluids includes a syringe adapter including a housing having a first end and a second end with the first end configured to be secured to a first container, a cannula having a first end and a second end with the second end positioned within the housing, and a seal arrangement positioned within the housing and movable within the housing where the seal arrangement includes a membrane. The system including a second component having a membrane and a connection member, with the second component configured to be received by the syringe adapter such that the membrane of the seal arrangement engages the membrane of the second component. The connection member configured to engage a portion of the housing of the syringe adapter to secure the second component to the syringe adapter when the second component is received by the syringe adapter.

The connection member may be a projection extending radially outward from the second component, with the projection received by a recessed portion of the housing of the syringe adapter to secure the second component to the syringe adapter when the second component is received by the syringe adapter. The projection may be semi-spherical. The projection may be a plurality of semi-spherical spaced-apart projections. The seal arrangement may be a collet having a first end and a second end, with at least a portion of the collet received within the housing and the collet including a body and a locking member connected to the body. The body of the collet defining a passageway that receives the membrane of the seal arrangement. The collet may be movable from a first position where the locking member is open to receive a mating connector to a second position where radially outward movement of the locking member is restricted. The second component may be a collet interface surface configured to receive and engage the locking member of the collet. The locking member may be arcuate-shaped and resilient, with the locking member connected to the body via a plurality of arms. The second component may be a patient connector having a first end and a second end, with the patient connector having a body defining a passageway and the second end of the patient connector configured to be secured to a patient IV line.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein:

FIG. 7A is a front view of a first membrane according to one aspect of the present invention.

FIG. 7B is a cross-sectional view of the first membrane of FIG. 7A.

FIG. 8A is a front view of a first membrane according to one aspect of the present invention.

FIG. 8B is a cross-sectional view of the first membrane of FIG. 8A.

FIG. 9A is a front view of a first membrane according to one aspect of the present invention.

FIG. 9B is a cross-sectional view of the first membrane of FIG. 9A.

FIG. 10A is a front view of a first membrane according to one aspect of the present invention.

FIG. 10B is a cross-sectional view of the first membrane of FIG. 10A.

FIG. 31 is a cross-sectional view of the system of FIG. 30.

FIG. 32 is a cross-sectional view of the system of FIG. 30, showing a patient connector secured to a syringe adapter with a lock mechanism in an unlocked position.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
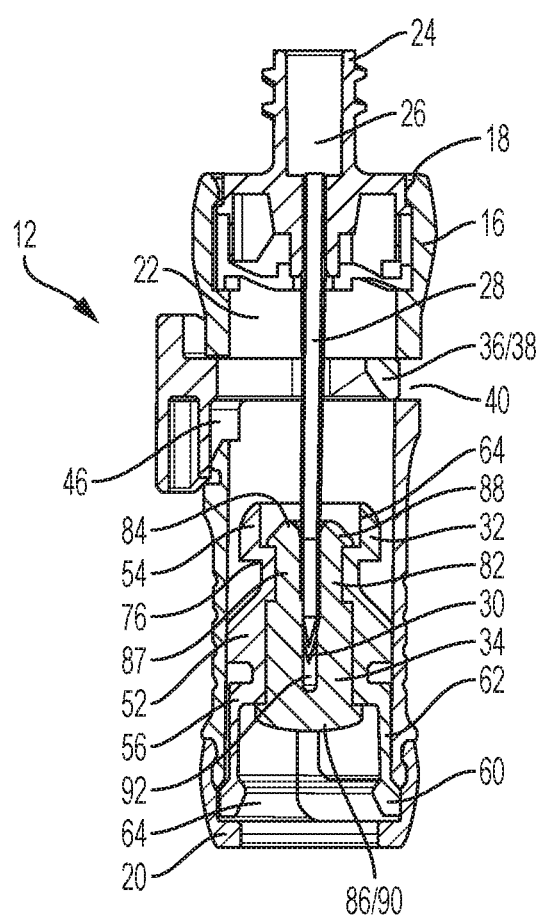
FIG. 1 is a cross-sectional view of a syringe adapter according to one aspect of the present invention.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Hence, specific dimensions and other physical characteristics related to the aspects disclosed herein are not to be considered as limiting.

Referring to FIG. 1, a syringe adapter 12 according to one aspect of the present invention is shown. The syringe adapter 12 is one component of a system for the closed transfer of fluids. In particular, the syringe adapter 12 is configured to connect to a syringe (not shown) to another medical device or fluid container. The medical device can be, for example, a patient line, vial adapter, fluid container, or infusion adapter. In other examples, the container can be a medical vial, syringe barrel, IV bag, or similar container for holding a fluid to be administered to a patient. The syringe adapter 12 can be used to facilitate the closed transfer of fluids between the syringe and medical device or fluid container. The syringe adapter 12 is similar to and operates in a similar manner as the syringe adapter shown and described in United States Patent Application Publication No. 2015/0297454, which is hereby incorporated by reference in its entirety.

Referring again to FIG. 1, the syringe adapter 12 includes a housing 16 having a first end 18 and a second end 20 and defining an interior space 22. The first end 18 of the housing 16 of the syringe adapter 12 includes a syringe attachment 24, such as a female luer connector, that defines a passageway 26. Although a female luer connector is shown for connection with a corresponding male luer connector of a syringe (not shown), other suitable connection arrangements may be utilized for connection to a syringe, container, or any other medical device. A cannula 28 having a distal end 30 is secured to the syringe attachment 24 and in fluid communication with the passageway 26 of the syringe attachment 24. The syringe adapter 12 further includes a seal arrangement positioned within the housing 16 of the syringe adapter 12. The seal arrangement includes a collet 32 that receives a first membrane 34. The collet 32 is configured to move within the interior space 22 of the housing 16 of the syringe adapter 12 as discussed in more detail below. The housing 16 of the syringe adapter 12 may include structure to enhance gripping of the syringe adapter 12 by a user. Additional or alternative grip structures and surfaces may be provided to assist a user in gripping the body of the syringe adapter 12.

The syringe adapter 12 includes a first connection interface 36 positioned intermediate the first and second ends 18, 20 of the housing 16 of the syringe adapter 12 that includes a lock member 38 that is received within a transverse opening 40 in the housing 16 of the syringe adapter 12. The lock member 38 is configured to move between a closed position and an open position. The lock member 38 further includes a cantilever spring 46 that extends in a longitudinal direction of the syringe adapter 12. The lock member 38 is configured to engage a cam surface that extends radially outward from the housing 16 of the syringe adapter 12. In particular, the lock member 38 is configured to be provided in the closed position, where a portion of the lock member 38 adjacent to a central opening of the lock member 38 is positioned within the interior space 22 of the syringe adapter 12 when no external forces are applied to the lock member 38. When the lock member 38 is moved to the open position where central opening of the lock member 38 is aligned with the interior space 22 of the syringe adapter 12 or does not create an interference or barrier to objects being inserted into the interior space 22, the cantilever spring 46 engages the cam surface to create a biasing force that urges the lock member 38 back towards the closed position. Accordingly, when the lock member 38 is moved to the open position, the lock member 38 will be urged back to the closed position when the external force acting on the lock member 38 is released. Although the lock member 38 is shown with the cantilever spring 46, any other suitable biasing member may be provided including, but not limited to, compression springs, extension springs, elastomeric material, etc.

Figure 3:
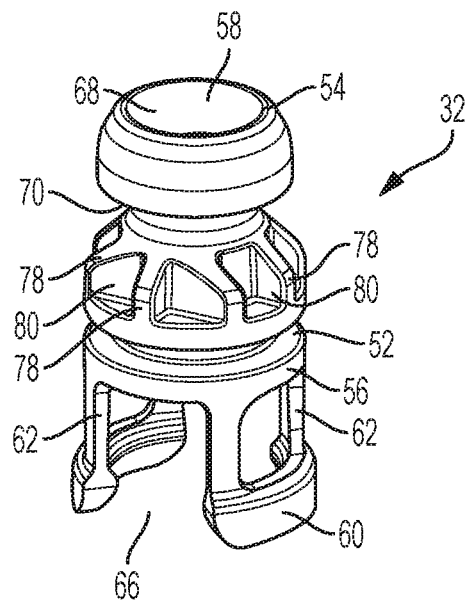
FIG. 3 is a perspective view of a collet according to one aspect of the present invention.
Figure 4:
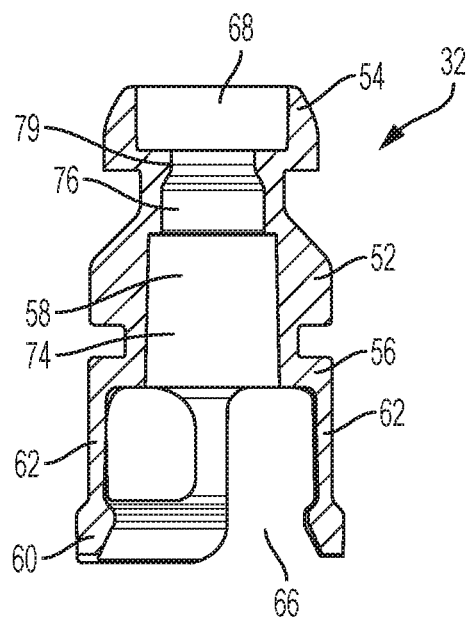
FIG. 4 is a cross-sectional view of the collet of FIG. 3.

Referring to FIGS. 1 and 3, the collet 32 has a body 52 with a first end 54 and a second end 56. The body 52 defines a passageway 58 that extends through the body 52. The body 52 is generally cylindrical, although other suitable shaped collets may be utilized. The collet 32 further includes a locking member 60 connected to the body 52 of the collet 32. The collet 32 is movable from a first position where the locking member 60 is open to receive a mating connector, such as a patient connector, to a second position where radially outward movement of the locking member 60 is restricted. The locking member 60 is connected to the body 52 via a plurality of arms 62. The locking member 60 is arcuate and resilient as a result of the connection of the locking member 60 to the body 52 via the plurality of arms 62. More specifically, the plurality of arms 62 are flexible and allow the locking member 60 to expand radially outward or radially inward. In one aspect, the locking member 60 is configured to expand radially outward when a mating connector, such as a patient connector, is inserted into the locking member 60 and subsequently moving radially inward as the collet 32 is transitioned from the first position to the second position. Alternatively, the locking member 60 may not move radially inward or outward when a mating connector is inserted into the locking member 60 and may subsequently move radially inward as the collet 32 is transitioned from the first position to the second position. The second end 20 of the housing 16 of the syringe adapter 12 defines an annular recess 64 adjacent to the interior space 22 that receives the locking member 60 when the collet 32 is in the first position. The annular recess 64 of the housing 16 provides the space for the locking member 60 to expand radially outward. When the collet 32 is transitioned from the first position to the second position, the collet 32 moves axially toward the first end 18 of the syringe adapter 12 with the locking member 60 being biased radially inward due to the engagement of the locking member 60 with the housing 16 of the syringe adapter 12.

As shown in FIG. 3, the locking member 60 of the collet 32 defines a pair of openings 66 that extend in a direction perpendicular to a longitudinal axis of the collet 32. The openings 66 bifurcate the locking member 60 into two arcuate portions that are each connected to the body 52 of the collet 32 by two arms 62. However, other suitable arrangements and shapes for the collet 32 and the locking member 60 may be utilized. The locking member 60 of the collet 32 protrudes radially inward and radially outward relative to the plurality of arms 62.

Referring again to FIGS. 1 and 3, the body 52 of the collet 32 includes a second connection interface 70 that is configured to mate with and lock with the first connection interface 36 of the syringe adapter 12. The second connection interface 70 is defined by the body 52 of the collet 32. The first end 54 of the collet 32 is configured to be received within the interior space 22 of the syringe adapter 12 when the lock member 38 of the first connection interface 36 is in the open position and restricted from moving within the interior space 22 of the syringe adapter 12 when the lock member 38 is in the closed position. When the second connection interface 70 is fully mated to the first connection interface 36, the lock member 38 of the first connection interface 36 is configured to be in the closed position to lock the first connection interface 36 from longitudinal and transverse movement relative to the second connection interface 70, but still allowing rotational movement relative thereto.

Referring to FIG. 1, the passageway 58 of the body 52 of the collet 32 includes a first counterbore 68, a second counterbore 74, positioned opposite the first counterbore 68, and an intermediate portion 76 positioned between the first and second counterbores 68, 74.

Referring to FIG. 3, the body of the collet 32 also includes a plurality of ribs 78 positioned intermediate the first end 54 and the second end 56. The ribs 78 extending longitudinally, although other suitable configurations may be utilized. A plurality of recesses 80 are positioned between adjacent ribs 78.

Referring to FIGS. 2-6, in one aspect of the present invention, the passageway 58 of the body of the collet 32 includes a narrowed portion 79 configured to compress a portion of the first membrane 34. In one aspect, the intermediate portion 76 of the passageway 58 of the body 52 of the collet 32 includes the narrowed portion 79. The narrowed portion 79 of the passageway 58 has a smaller diameter than a remaining portion of the intermediate portion 76 of the passageway 58.

Figure 2:
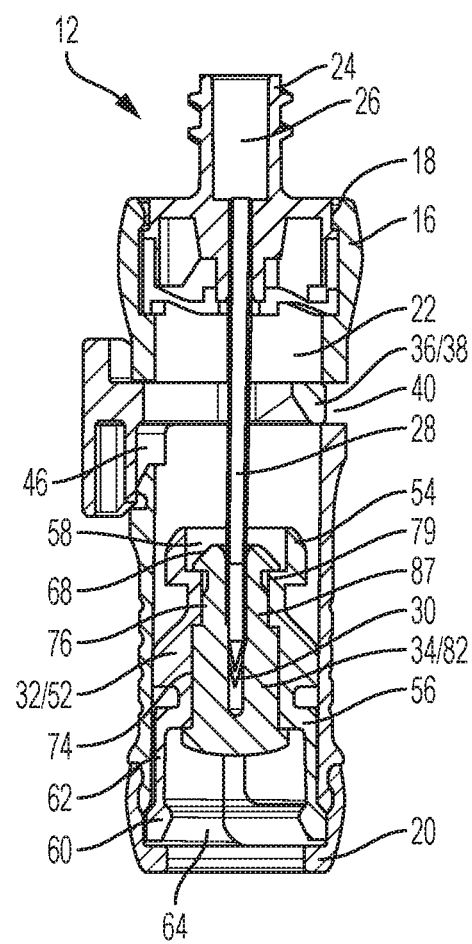
FIG. 2 is a cross-sectional view of a syringe adapter according to one aspect of the present invention.
Figures 5, 6:
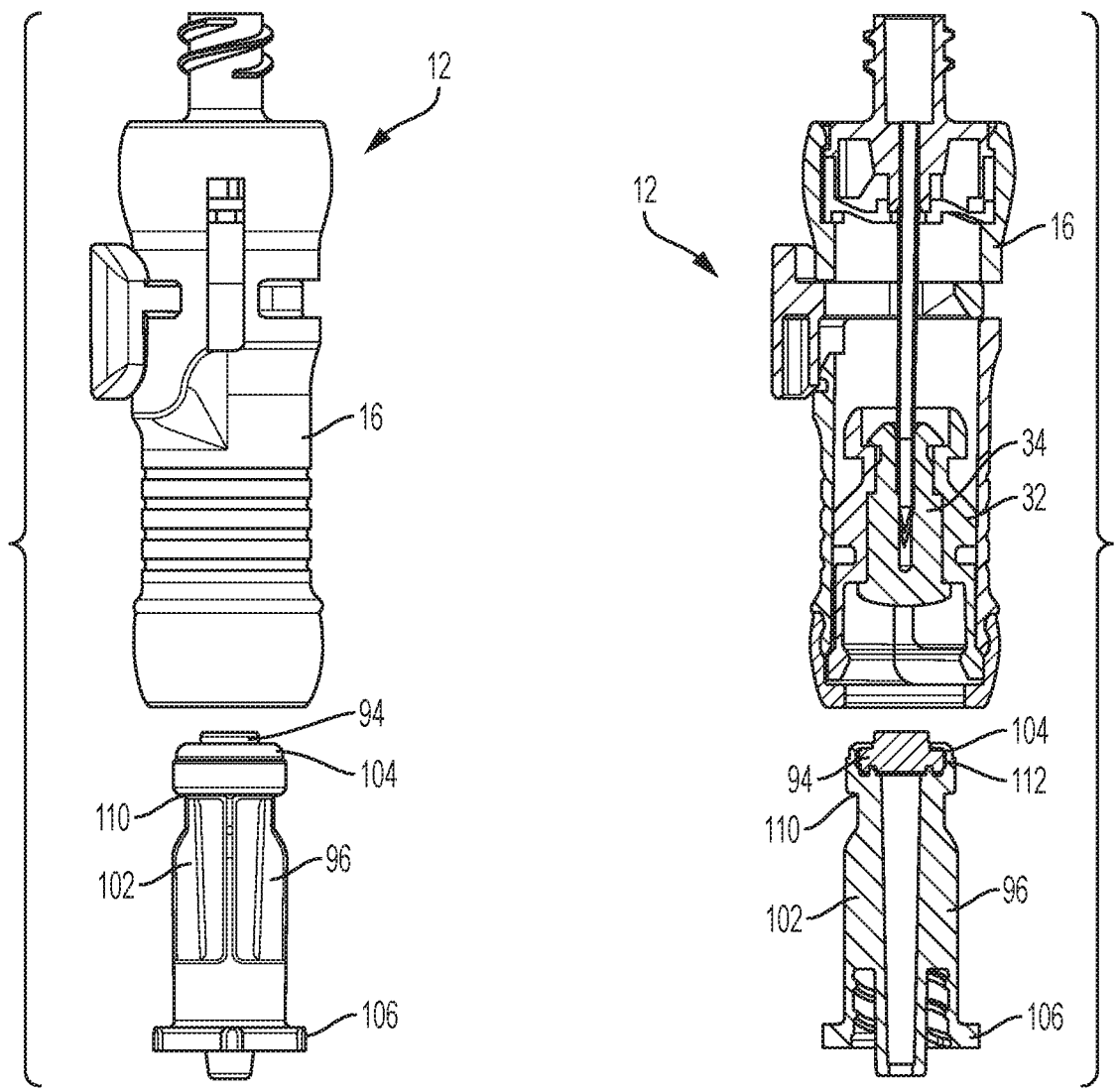
FIG. 5 is a front view of a system for the closed transfer of fluids according to one aspect of the present invention.
FIG. 6 is a cross-sectional view of the system of FIG. 5.
Figure 11A:
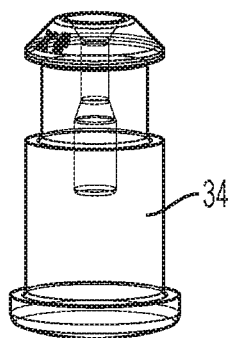
FIG. 11A is a front view of a first membrane according to one aspect of the present invention.

Referring to FIGS. 2 and 6, the first membrane 34 includes a body 82 having a first end 84 and a second end 86. The first end 84 and the second end 86 of the body 82 of the first membrane 34 include a first head portion 88 and a second head portion 90, respectively. The body 82 of the first membrane 34 defines a passageway 92 extending from the first end 84 towards the second end 86 of the body 82. The passageway 92 terminates at a position intermediate the first and second ends 84, 86 of the body 82. The body 82 of the first membrane 34 also defines an annular recessed portion 87 positioned intermediate the first and second ends 84, 86. The body 82 of the first membrane 34 is received by the passageway 58 of the collet 32 and is secured to the collet 32. The first head portion 88 of the first membrane 34 engages the first counterbore 68 of the collet 32. The second head portion 90 extends beyond the passageway 58 of the body 52 of the collet 32 with the second head portion 90 engaging the body 52 of the collet 32. The annular recessed portion 87 of the first member 34 is received by the intermediate portion 76 of the collet 32 with the narrowed portion 79 engaging and compressing the annular recessed portion 87 of the first member 34.

The second head portion 90 defines a convex surface, although other suitable membrane arrangements may be provided as discussed in more detail below. The cannula 28 is received within the passageway 92 of the first membrane 34 with the distal end 30 of the cannula 28 positioned within the passageway 92 when the collet 32 is in the first position. The distal end 30 of the cannula 28 is configured to pierce the first membrane 34 and extend through the first membrane 34 when the collet 32 is transitioned from the first position to the second position. The first membrane 34 is configured to engage and seal an intermediate portion of the cannula 28 during use of the syringe adapter 12 to maintain a sealed and leak-free connection with a mating component.

Upon engagement of the first membrane 34 by a corresponding membrane during use, such as a second membrane 94 from the patient connector 96, a vial adapter, or IV bag spike, the collet 32 is configured to move toward the first end 18 of the syringe adapter 12 and transition from the first position to the second position such that the distal end 30 of the cannula 28 pierces the first membrane 34 to place the syringe adapter 12 in fluid communication with corresponding devices secured to the syringe adapter 12. When the collet 32 is returned to the first position, the first membrane 34 can be disengaged from the corresponding membrane thereby positioning the distal end 30 of the cannula 28 within the passageways 58, 92 of the collet 32 and the first membrane 34. Such an arrangement shields the distal end 30 of the cannula 28 to prevent accidental needle sticks and also prevents the leakage of any fluid during transfer of fluids when using the syringe adapter 12.

Referring to FIGS. 5 and 6, the patient connector 96 includes a body 102 having a first end 104 and a second end 106 and defining a passageway 108 that extends therethrough. The first end 104 of the patient connector 96 also includes a collet interface 110. The collet interface 110 is defined by a portion of the body 102 of the patient connector 96 that is recessed relative to the first end 104 of the body 102 of the patient connector 96. The first end 104 of the body 102 of the patient connector 96 also includes a membrane seat 112 that receives a second membrane 94. As discussed above in connection with the syringe adapter 12, the second membrane 94 of the patient connector 96 is configured to engage the first membrane 34 of the syringe adapter 12 and provide a substantially leak-free connection with the syringe adapter 12 during fluid transfer. The second end 106 of the patient connector 96 includes an IV line attachment, such as a male luer connector, although any other suitable connection arrangement may be utilized.

Referring to FIGS. 2 and 6, as discussed above, the narrowed portion 79 of the passageway of the body 52 of the collet 32 compresses the first membrane 34. In particular, the narrowed portion 79 compresses the annular recessed portion 89 of the first membrane 34. During use of the syringe adapter 10, back pressure acting on the first membrane 34 could potentially unseat the first membrane 34 from the collet 32. The narrowed portion 79 acts as a back pressure resistance feature by applying additional compression between the collet 32 and the first membrane 34.

Figure 12A:
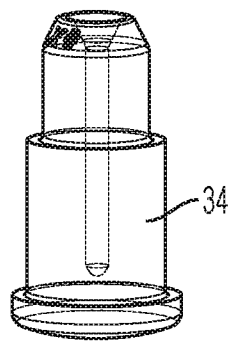
FIG. 12A is a front view of a first membrane according to one aspect of the present invention.
Figure 13A:
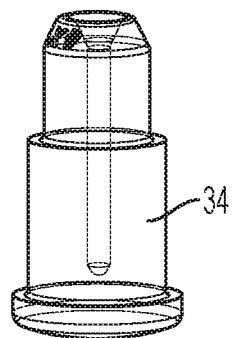
FIG. 13A is a front view of a first membrane according to one aspect of the present invention.
Figure 11B:
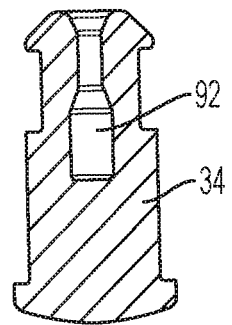
FIG. 11B is a cross-sectional view of the first membrane of FIG. 11A.
Figure 12B:
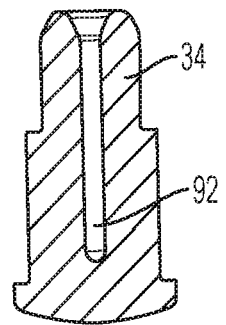
FIG. 12B is a cross-sectional view of the first membrane of FIG. 12A.
Figure 13B:
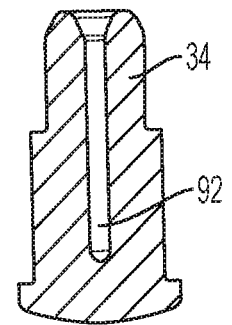
FIG. 13B is a cross-sectional view of the first membrane of FIG. 13A.
Figure 14A:
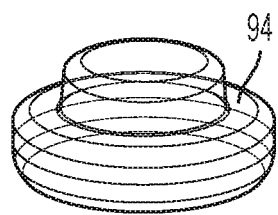
FIG. 14A is a front view of a second membrane according to one aspect of the present invention.
Figure 15A:
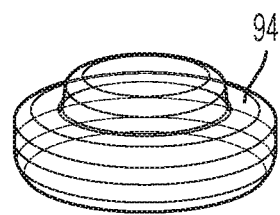
FIG. 15A is a front view of a second membrane according to one aspect of the present invention.
Figure 14B:
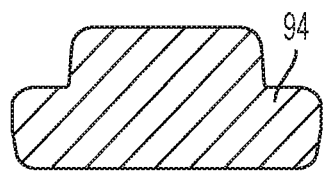
FIG. 14B is a cross-sectional view of the second membrane of FIG. 14A.
Figure 15B:
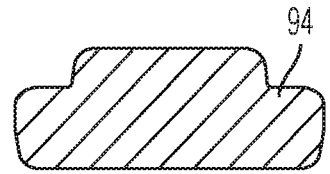
FIG. 15B is a cross-sectional view of the second membrane of FIG. 15A.
Figure 16A:
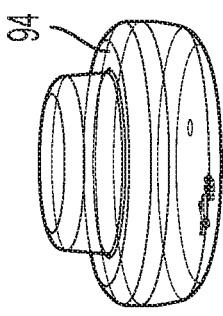
FIG. 16A is a front view of a second membrane according to one aspect of the present invention.
Figure 16B:
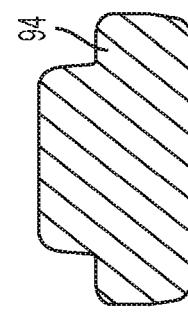
FIG. 16B is a cross-sectional view of the second membrane of FIG. 16A.
Figure 17A:
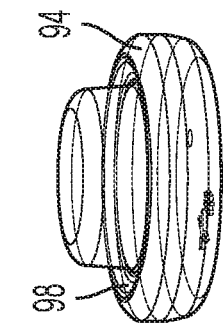
FIG. 17A is a front view of a second membrane according to one aspect of the present invention.
Figure 17B:
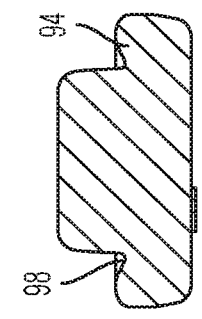
FIG. 17B is a cross-sectional view of the second membrane of FIG. 17A.
Figure 18A:
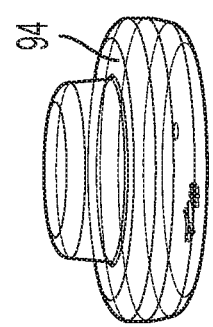
FIG. 18A is a front view of a second membrane according to one aspect of the present invention.
Figure 18B:
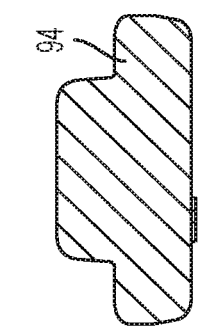
FIG. 18B is a cross-sectional view of the second membrane of FIG. 18A.
Figure 19A:
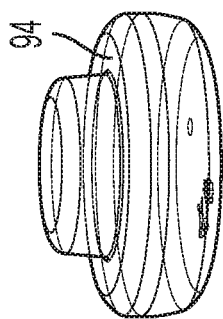
FIG. 19A is a front view of a second membrane according to one aspect of the present invention.
Figure 19B:
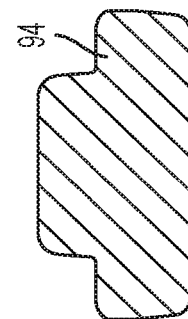
FIG. 19B is a cross-sectional view of the second membrane of FIG. 19A.
Figure 20:
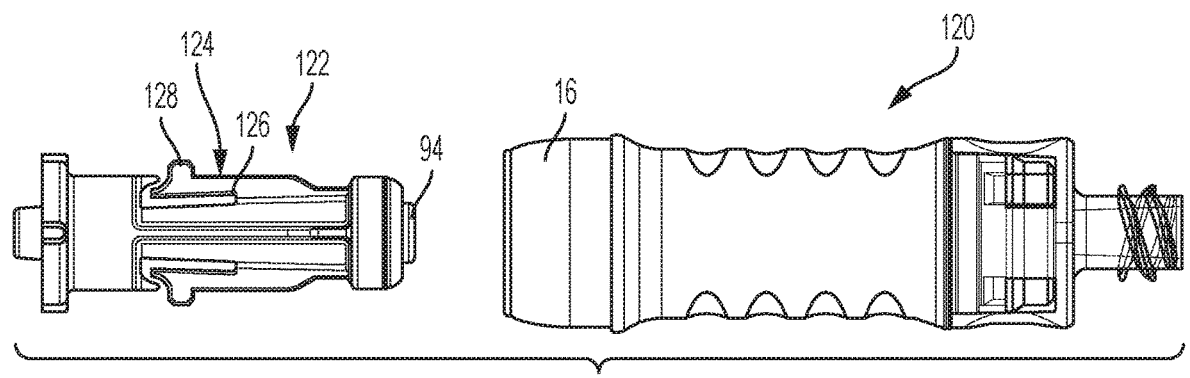
FIG. 20 is a front view of a system for the closed transfer of fluids according to one aspect of the present invention.

Referring to FIGS. 7A-13B, further aspects of the first membrane 34 are shown. In particular, various shapes, configurations, and cavities may be utilized for the first membrane 34. The geometries shown in FIGS. 7A-13B may be pushed or pulled into a mating component and retained without the need for secondary assembly processes or multi-piece housings. The passageway 92 of the first membrane may include various shapes, lengths, widths, and configurations. Further, as shown in FIGS. 12-13B, the first end 84 of the first membrane 34 may not include a head portion or radial projections.

Referring to FIGS. 14A-19B, further aspects of the second membrane 94 are shown. In particular, various shapes and configurations may be utilized for the second membrane 94. As shown in FIGS. 17A and 17B, the second membrane 94 may include an annular recess 98.

Referring to FIGS. 21-24, a syringe adapter 120 and patient connector 122 according to a further aspect of the present invention is shown. The syringe adapter 120 is similar to the syringe adapter 12 shown in FIG. 1 and operates in a similar manner. The syringe adapter 120 and patient connector 122 of FIGS. 21-24, however, include a different connection arrangement. In particular, rather than providing the first and second connection interfaces 36, 70, the patient connector 122 includes a locking mechanism 124 having a biasing member 126 and an engagement member 128 positioned on the biasing member 126. The engagement member 128 is configured to engage a portion of the housing 16 of the syringe adapter 120 to secure the patient connector 122 to the syringe adapter 120 when the patient connector 122 is received by the syringe adapter 120. Although the locking mechanism 124 is shown in connection with the patient connector 122, the locking mechanism 124 may be provided on any suitable component of a system for the closed transfer of fluids, including, but not limited to, vial adapters, infusion adapters, etc.

The biasing member 126 of the locking mechanism 124 is a cantilever arm, although other suitable biasing arrangements may be utilized. The engagement member 128 is a projection extending radially outwards from the patient connector 122, although other suitable projections may be utilized. The engagement member 128 is configured to engage a portion of the housing 16 of the syringe adapter 120 to bias the engagement member 128 radially inward via the cantilever arm during insertion of the patient connector 122 into the syringe adapter 120. The engagement member 128 is also configured to return to a non-biased position when the patient connector 122 has been fully inserted into the syringe adapter 120 to secure the patient connector 122 to the syringe adapter 120. Accordingly, upon inserting the patient connector 122 into the housing 16 of the syringe adapter 120, the biasing member 126 is deflected radially inward through engagement of the engagement member 128 with the housing 16 of the syringe adapter 120. Once fully inserted, the biasing member 126 returns to the non-biased position with the engagement member 128 retaining the patient connector 122 in the syringe adapter 120 with the collet 32 engaged with the collet interface 110 of the patient connector 122. To remove the patient connector 122, a user applies an axial force to the patient connector 122 in a direction away from the syringe adapter 120 such that the biasing member 126 is again deflected radially inward through engagement of the engagement member 128 with the housing 16 of the syringe adapter 120 until the engagement member 128 is axially displaced beyond the housing 16 of the syringe adapter 120. The collet 32 will also release from the patient connector 122 in the same manner as discussed above in connection with syringe adapter 12.

Figure 21:
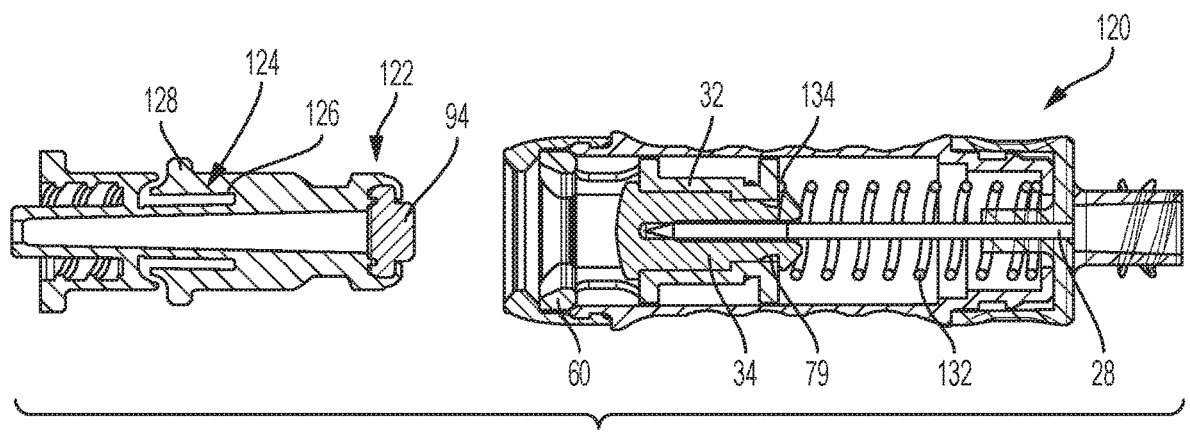
FIG. 21 is a cross-sectional view of system shown in FIG. 20.
Figure 22:
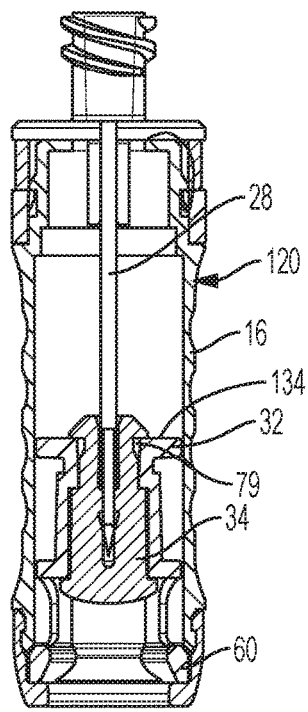
FIG. 22 is a cross-sectional view of a syringe adapter according to one aspect of the present invention.
Figure 23:
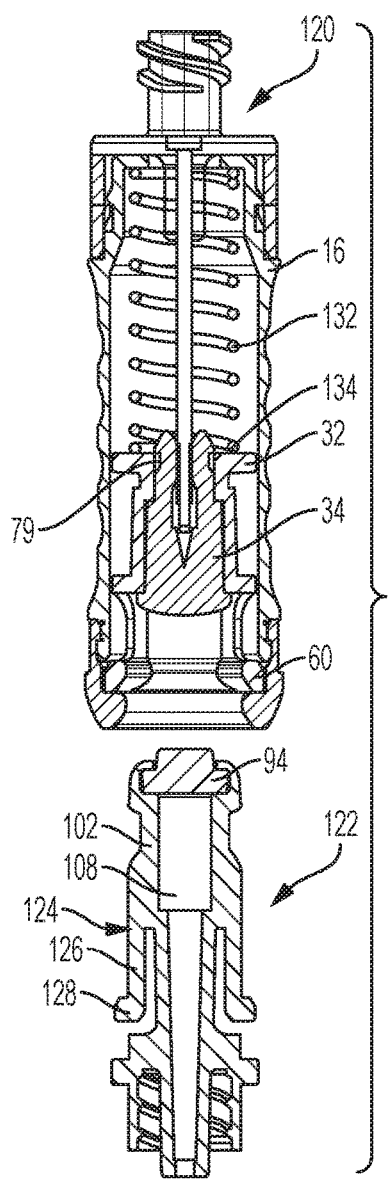
FIG. 23 is a cross-sectional view of a syringe adapter according to one aspect of the present invention.
Figure 24:
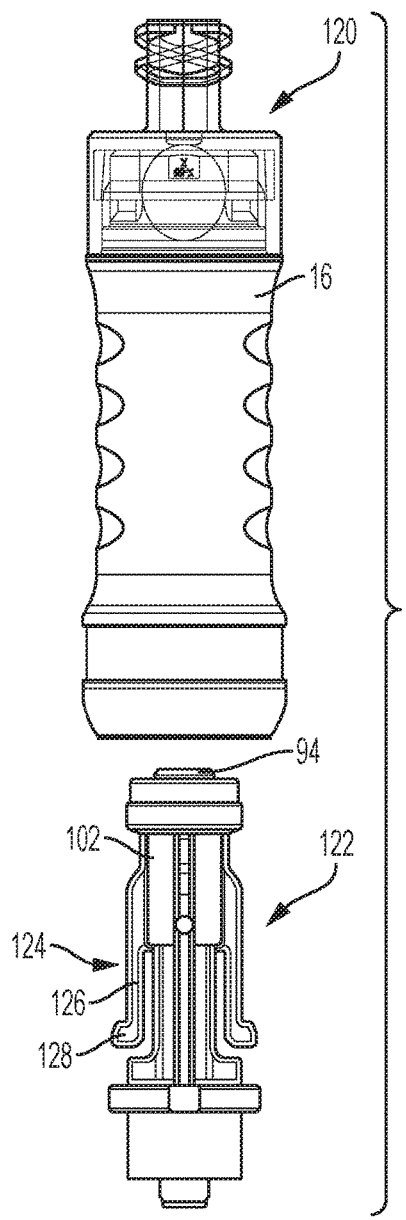
FIG. 24 is a front view of a syringe adapter according to one aspect of the present invention.
Figure 25:
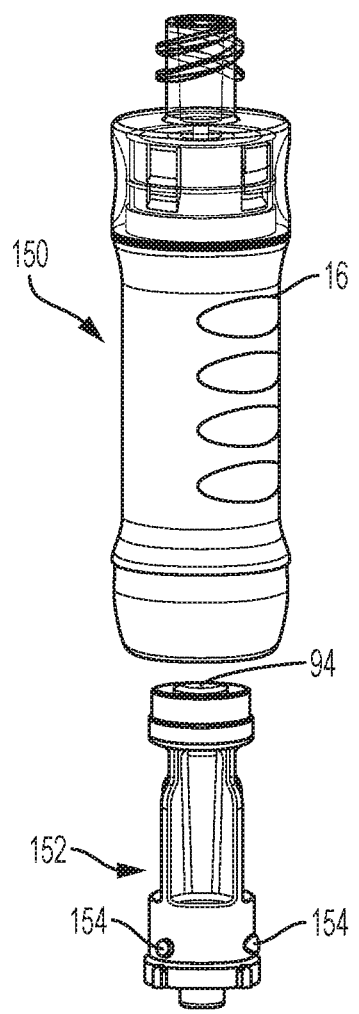
FIG. 25 is a front view of a system for the closed transfer of fluids according to one aspect of the present invention.
Figure 26:
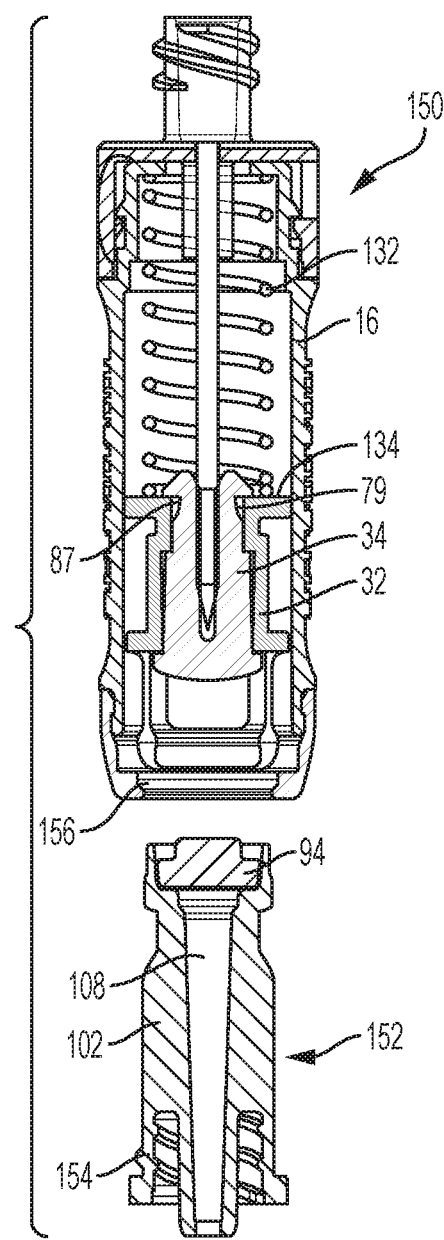
FIG. 26 is a cross-sectional view of the system of FIG. 25.

Referring to FIGS. 21 and 23, the syringe adapter 120 may also include a collet drive member 132 configured to bias the collet 32 toward the second end 20 of the syringe adapter 120 to maintain the collet 32 in the first position. The syringe adapter 120 operates in the same manner as discussed above in connection with syringe adapter 12, but the collet drive member 132 requires a user to overcome the biasing force of the collet drive member 132 to move the collet 32 from the first position to the second position when the syringe adapter 120 is mated with a mating connector, such as the patient connector 122. The collet drive member 132 may be a spring, although other suitable biasing arrangements may be utilized. Further, as shown in FIGS. 21-23, the collet 32 may not include the first counterbore 68 with the first end 54 of the collet defining a planar surface 134.

Referring to FIGS. 25-29, a syringe adapter 150 and patient connector 152 according to a further aspect of the present invention is shown. The syringe adapter 150 is similar to the syringe adapter 12 shown in FIG. 1 and operates in a similar manner. The syringe adapter 150 and patient connector 152 of FIGS. 25-29, however, include a different connection arrangement. In particular, rather than providing the first and second connection interfaces 36, 70, the patient connector 152 includes a connection member 154. The connection member 154 is configured to engage a portion of the housing 16 of the syringe adapter 150 to secure the patient connector 152 to the syringe adapter 150 when the patient connector 152 is received by the syringe adapter 150. Although the connection member 154 is shown with the patient connector 152, the connection member 154 may be provided on any suitable component of a system for the closed transfer of fluids, including, but not limited to, vial adapters, infusion adapters, etc.

Figure 27:
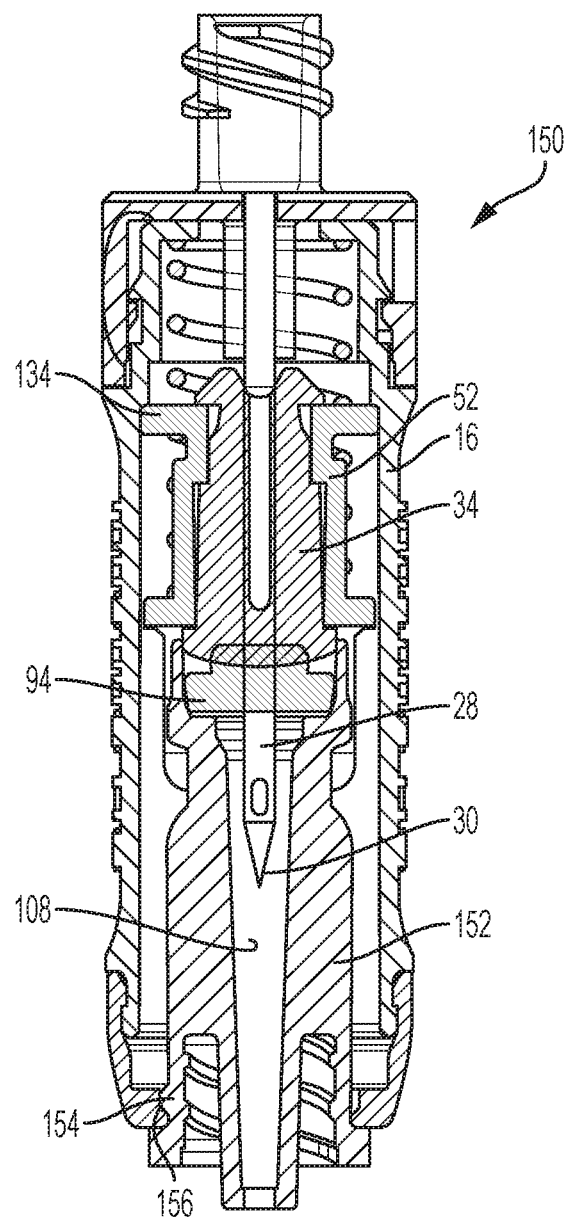
FIG. 27 is a cross-sectional view of the system of FIG. 25, showing a patient connector secured to a syringe adapter.
Figure 28:
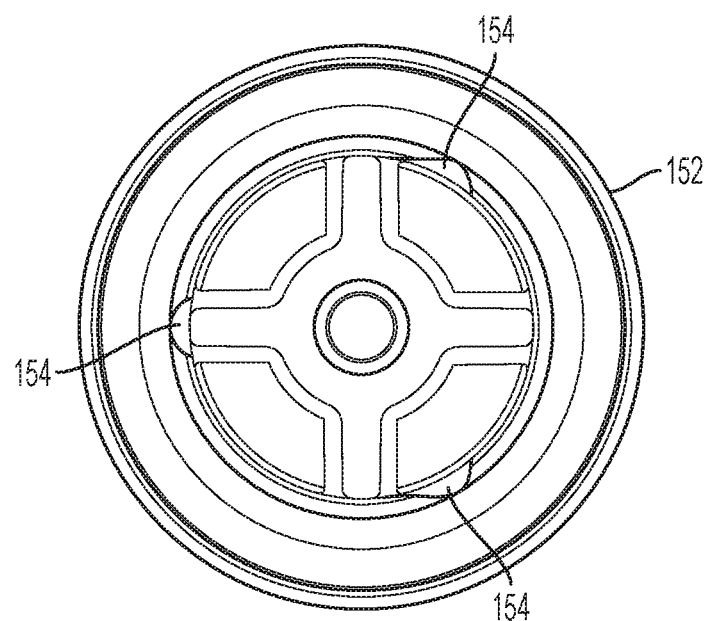
FIG. 28 is a top view of the patient connector of FIG. 25 according to one aspect of the present invention.
Figure 29:
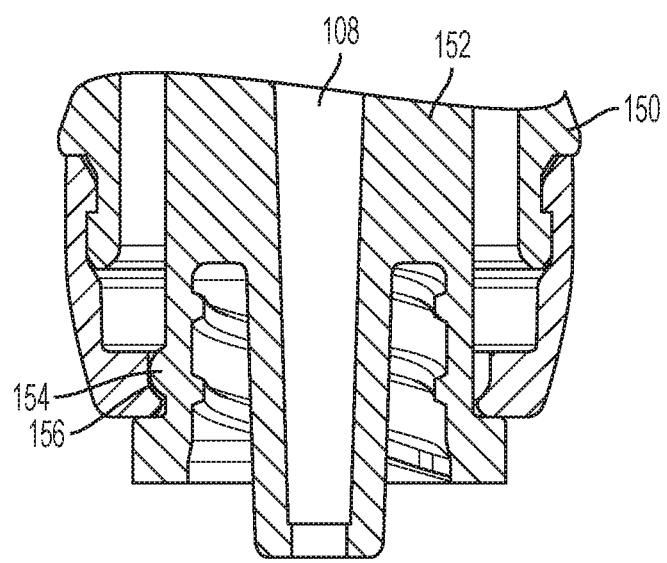
FIG. 29 is an enlarged cross-sectional view of the system of FIG. 25, showing a patient connector secured to a syringe adapter.
Figure 30:
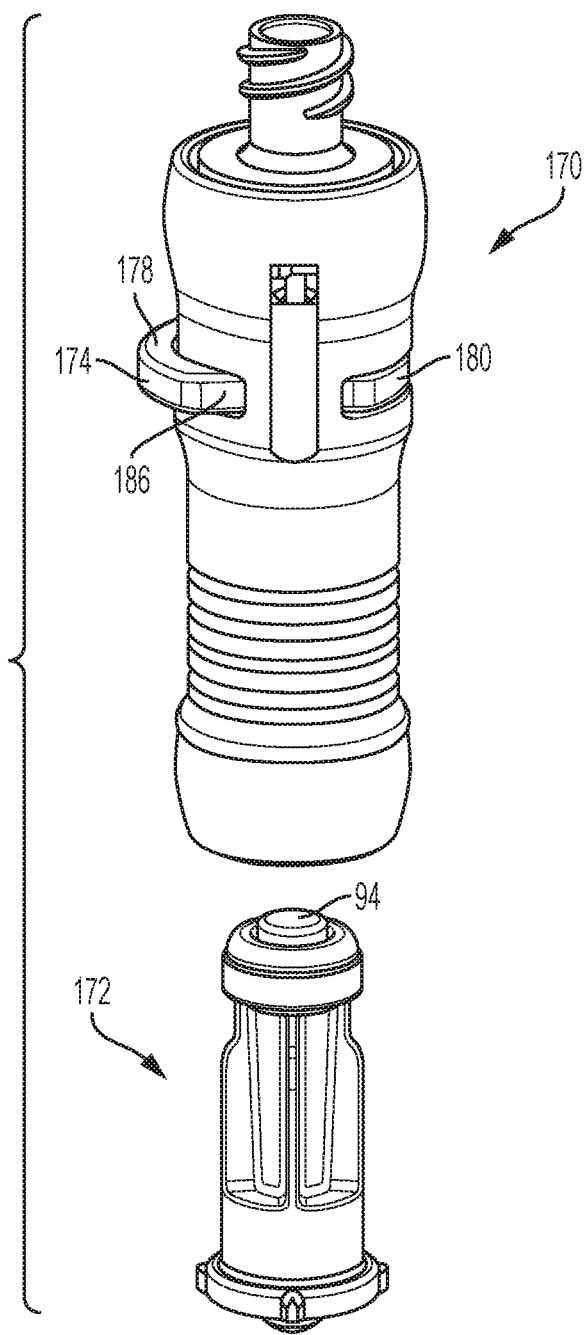
FIG. 30 is a perspective view of a system for the closed transfer of fluids according to one aspect of the present invention.
Figure 33:
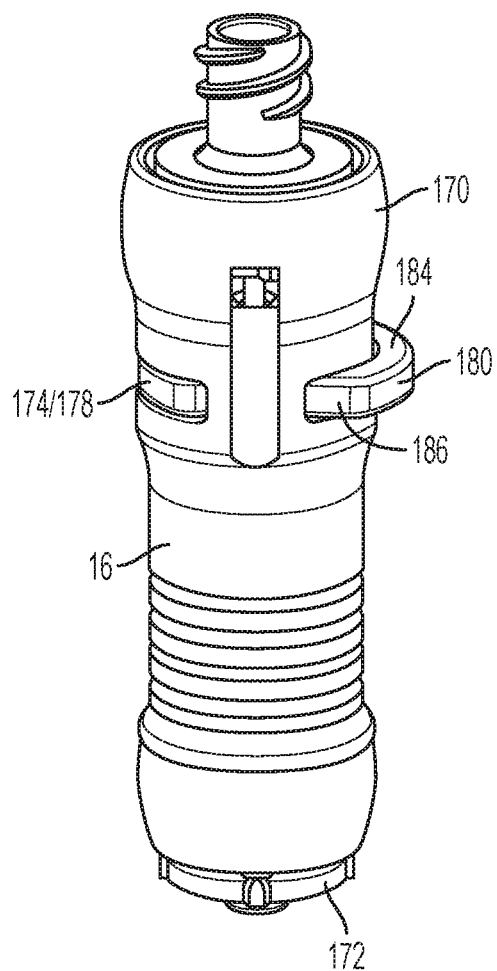
FIG. 33 is a perspective view of the system of FIG. 30, showing a patient connector secured to a syringe adapter with a lock mechanism in a locked position.
Figure 34:
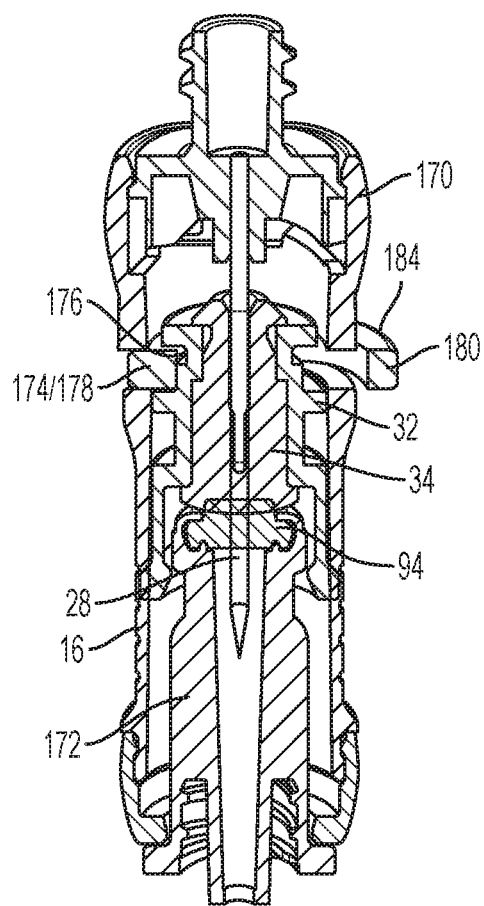
FIG. 34 is a cross-sectional view of the system of FIG. 30, showing a patient connector secured to a syringe adapter with a lock mechanism in a locked position.
Figure 35:
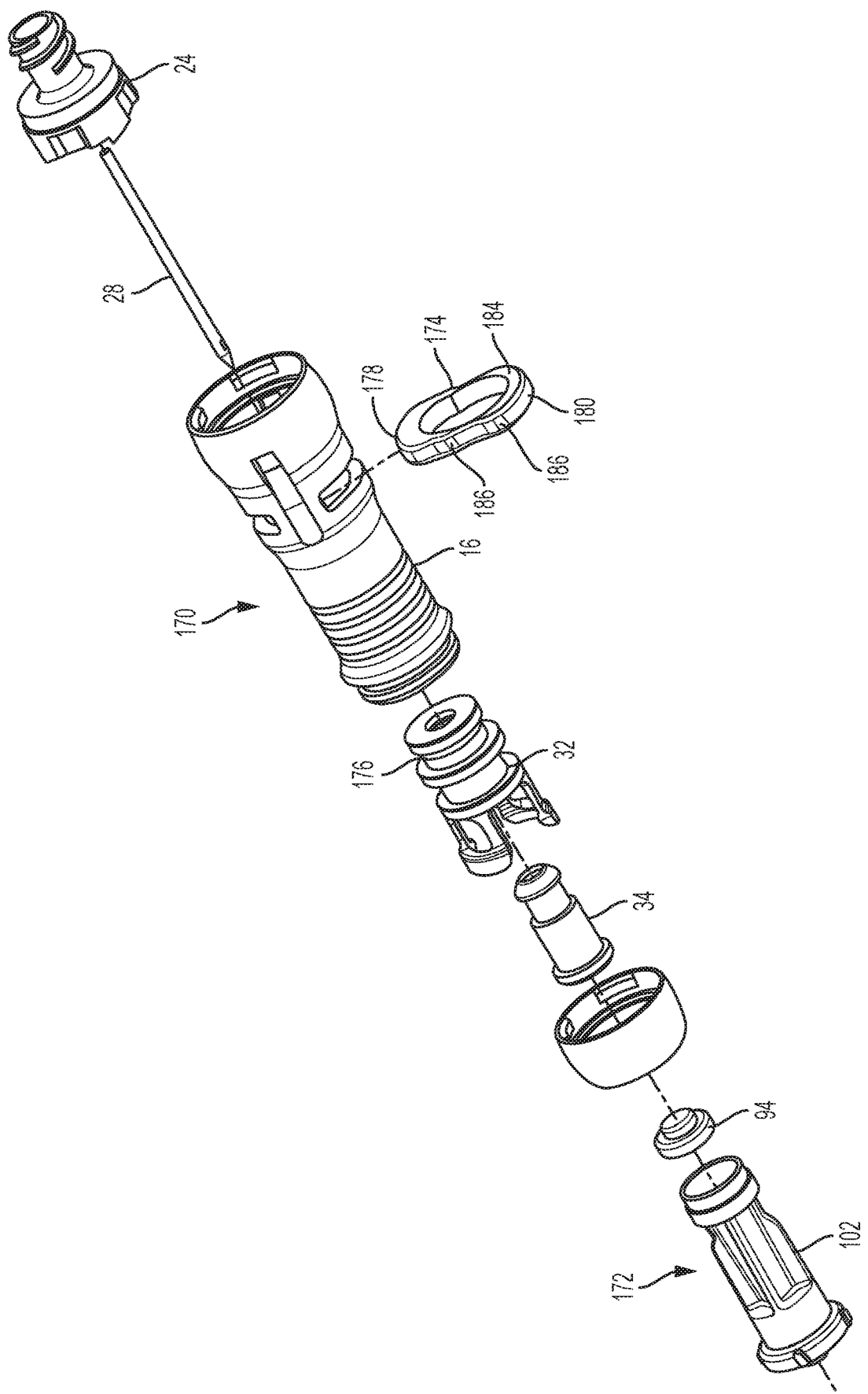
FIG. 35 is an exploded, perspective view of the system of FIG. 30 according to one aspect of the present invention.

The connection member 154 is a projection extending radially outward from the patient connector 152. The connection member 154 is received by a recessed portion 156 of the housing 16 of the syringe adapter 150 to secure the patient connector 152 to the syringe adapter 150 when the patient connector 152 is received by the syringe adapter 150. The connection member 154 is semi-spherical, although other suitable shapes and configurations may be utilized. As shown in FIG. 28, three equally spaced-apart connection members 154 are provided on the patient connector 152, although one or more connection members 154 may be provided. Upon inserting the patient connector 152 into the housing 16 of the syringe adapter 150, the second membrane 94 of the patient connector 152 engages the first membrane 34 of the collet 32 and moves the collet 32 to the second position as described above in connection with syringe adapter 12. As shown in FIGS. 27 and 29, however, when the collet 32 is transitioned to the second position, the connection member(s) 154 engage the housing 16 of the syringe adapter 150 and are received within the recessed portion 156 of the housing 16 to further secure the patient connector 152 to the syringe adapter 150. To remove the patient connector 152, a user applies an axial force to the patient connector 152 in a direction away from the syringe adapter 150 such that connection member(s) 154 snap out of the recessed portion 156 of the housing 16 of the syringe adapter 150. The collet 32 will also release from the patient connector 152 in the same manner as discussed above.

Referring to FIGS. 30-35, a syringe adapter 170 and patient connector 172 according to a further aspect of the present invention is shown. The syringe adapter 170 is similar to the syringe adapter 12 shown in FIG. 1 and operates in a similar manner. The syringe adapter 170 of FIGS. 25-29, however, includes a different connection arrangement. The syringe adapter 170 includes a lock mechanism 174 movable between an unlocked position (shown in FIGS. 31 and 32) and a locked position (shown in FIGS. 33 and 34). The collet 32 includes a lock interface 174 that is configured to engage the lock mechanism 174 when the collet 32 is in the second position and when the lock mechanism 174 is in the locked position. The lock mechanism 174 is disengaged from the lock interface 176 when the collet 32 is in the second position and when the lock mechanism 174 is in the unlocked position. The lock mechanism 174 is manually movable between the locked and unlocked positions by a user, although other suitable arrangements may be utilized.

The lock mechanism 174 has a first end 178 and a second end 180 and defines an opening 182 that is configured to receive the collet 32. When the lock mechanism 174 is in the unlocked position, the first end 178 of the lock mechanism 174 protrudes from the housing 16 and the second end 180 of the lock mechanism 174 is received within the housing 16. When the lock mechanism 174 is in the locked position, the first end 178 of the lock mechanism 174 is received within the housing 16 and the second end 180 of the lock mechanism 174 protrudes from the housing 16. The second end 180 of the lock mechanism includes an indicator 184. The indicator 184 may be a colored portion of the lock mechanism 174 that is different than the remaining portion of the lock mechanism 174. The colored portion may be a dominant color, such as red. The lock mechanism 174 is received within the transverse opening 40 of the housing 16 of the syringe adapter 170 and is retained within the housing 16 via retention portions 186 of the lock mechanism 174 positioned intermediate the first and second ends 178, 180 of the lock mechanism 174 that engage the housing 16.

As shown in FIG. 32, when the patient connector 172 is received within the syringe adapter 170 with the collet 32 moved to the second position, the collet 32 is received by the opening 182 of the lock mechanism 174. To maintain the collet 32 and the patient connector 172 in the second position, the lock mechanism 174 is transitioned to the locked position such that the lock mechanism 174 engages the lock interface 176 of the collet 32 with the indicator 184 providing an indication of the locked status of the syringe adapter 170.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A system for closed transfer of fluids comprising:
   a syringe adapter comprising:
      a housing having a first end and a second end, the first end configured to be secured to a first container;
      a cannula having a first end and a second end, the second end of the cannula positioned within the housing;
      a seal arrangement positioned within the housing and movable within the housing, the seal arrangement comprising a membrane; and
   a second component comprising a membrane and a locking mechanism, the second component configured to be received by the syringe adapter such that the membrane of the seal arrangement engages the membrane of the second component, the locking mechanism comprising a biasing member and an engagement member positioned on the biasing member, the engagement member configured to engage a portion of the housing of the syringe adapter to secure the second component to the syringe adapter when the second component is received by the syringe adapter.

2. The system of claim 1, wherein the biasing member of the locking mechanism comprises a cantilever arm and the engagement member comprises a projection extending radially outward from the second component, the projection configured to engage a portion of the housing to bias the projection radially inward via the cantilever arm during insertion of the second component into the syringe adapter, the projection configured to return to a non-biased position when the second component has been fully inserted into the syringe adapter to secure the second component to the syringe adapter.

3. The system of claim 1, wherein the seal arrangement comprises a collet having a first end and a second end, at least a portion of the collet received within the housing, the collet comprising a body and a locking member connected to the body, the body defining a passageway that receives the membrane of the seal arrangement, the collet is movable from a first position where the locking member is open to receive a mating connector to a second position where radially outward movement of the locking member is restricted.

4. The system of claim 3, wherein the biasing member of the locking mechanism comprises a cantilever arm and the engagement member comprises a projection extending radially outward from the second component, the projection configured to engage a portion of the housing to bias the projection radially inward via the cantilever arm during insertion of the second component into the syringe adapter, the projection configured to return to a non-biased position when the second component has been fully inserted into the syringe adapter to secure the second component to the syringe adapter.

5. The system of claim 4, wherein the second component comprises a collet interface surface configured to receive and engage the locking member of the collet.

6. The system of claim 4, wherein the locking member is arcuate-shaped and resilient, and wherein the locking member is connected to the body via a plurality of arms.

7. The system of claim 1, wherein the second component comprises a patient connector having a first end and a second end, the patient connector having a body defining a passageway, the second end of the patient connector configured to be secured to a patient IV line.

8. A system for closed transfer of fluids comprising:
   a syringe adapter comprising:
      a housing having a first end and a second end, the first end configured to be secured to a first container;
      a cannula having a first end and a second end, the second end of the cannula positioned within the housing;
      a seal arrangement positioned within the housing and movable within the housing, the seal arrangement comprising a membrane; and
   a second component comprising a membrane and a connection member, the second component configured to be received by the syringe adapter such that the membrane of the seal arrangement engages the membrane of the second component, the connection member configured to engage a portion of the housing of the syringe adapter to secure the second component to the syringe adapter when the second component is received by the syringe adapter, the connection member comprising a projection extending radially outward from the second component, the projection received by a recessed portion of the housing of the syringe adapter via a snap-fit mechanism to secure the second component to the syringe adapter when the second component is received by the syringe adapter, the projection comprising a plurality of projections.

9. The system of claim 8, wherein the plurality of projections are semi-spherical.

10. The system of claim 8, wherein the plurality of projections are semi-spherical spaced-apart projections.

11. The system of claim 8, wherein the seal arrangement comprises a collet having a first end and a second end, at least a portion of the collet received within the housing, the collet comprising a body and a locking member connected to the body, the body defining a passageway that receives the membrane of the seal arrangement, the collet is movable from a first position where the locking member is open to receive a mating connector to a second position where radially outward movement of the locking member is restricted.

12. The system of claim 11, wherein the second component comprises a collet interface surface configured to receive and engage the locking member of the collet.

13. The system of claim 11, wherein the locking member is arcuate-shaped and resilient, and wherein the locking member is connected to the body via a plurality of arms.

14. The system of claim 8, wherein the second component comprises a patient connector having a first end and a second end, the patient connector having a body defining a passageway, the second end of the patient connector configured to be secured to a patient IV line.

15. The system of claim 8, wherein, responsive to an axial force on the second component away from the syringe adapter, the projection of the connection member is configured to be released from the recessed portion of the housing.

16. The system of claim 8, wherein, when the second component is received by the syringe adapter, the projection engages the recessed portion.

17. The system of claim 8, wherein the projection comprises a plurality of equally spaced-apart projections.

18. The system of claim 17, wherein the plurality of projections comprises at least three projections.

* * * * *